US010896754B2

(12) United States Patent
An et al.

(10) Patent No.: US 10,896,754 B2
(45) Date of Patent: Jan. 19, 2021

(54) TROUBLESHOOTING SYSTEM FOR REMOTE PATIENT MONITORING (71) Applicant: Cardiac Pacemakers, Inc., St. Paul, MN (US)

(72) Inventors: Qi An, Blaine, MN (US); Kimberly Anne Eridon, Vadnais Heights, MN (US); Arwinder Pal Singh, St. Paul, MN (US); Pratik K. Pandya, Minneapolis, MN (US); Ranganathan Balasubramanian Iyer, Shoreview, MN (US); Viktoria A. Averina, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 86 days.

(21) Appl. No.: 16/239,379

(22) Filed: Jan. 3, 2019

(65) Prior Publication Data
US 2019/0206557 A1    Jul. 4, 2019

Related U.S. Application Data (60) Provisional application No. 62/613,687, filed on Jan. 4, 2018.

(51) Int. Cl.
*G16H 40/40* (2018.01)
*A61B 5/00* (2006.01)
(Continued)

(52) U.S. Cl.
CPC ........... *G16H 40/40* (2018.01); *A61B 5/0002* (2013.01); *A61B 5/0022* (2013.01); *A61N 1/37* (2013.01);
(Continued)

(58) Field of Classification Search
CPC .......... A61B 5/0002–0026; A61N 1/37–3718; G16H 10/10–65; G16H 40/00–67;
(Continued)

(56) References Cited

U.S. PATENT DOCUMENTS 5,752,976 A   5/1998 Duffin et al.
6,442,433 B1  8/2002 Linberg
(Continued)

FOREIGN PATENT DOCUMENTS

WO    03043494      5/2003
WO    2017139164   8/2017
WO    2019136230   7/2019

OTHER PUBLICATIONS

Piccini, Jonathan P. et al., "Progress toward the prevention and treatment of atrial fibrillation: A summary of the Heart Rhythm Society Research Forum on the Treatment and Prevention of Atrial Fibrillation, Washington, DC, Dec. 9-10, 2013," Heart Rhythm. Jan. 2015; 12(1) 44 pages.
(Continued)

*Primary Examiner* — Brendan Y Higa
(74) *Attorney, Agent, or Firm* — Pauly, DeVries Smith & Deffner LLC (57) ABSTRACT

The technology herein relates to a troubleshooting system for remote patient monitoring. A plurality of triggering conditions defines a data transmission error between a sensor and a remote location. A data transmission log is configured to receive characterization data defining each successful data transmission between a communicator and the remote location. An input user interface is configured to receive input from a user and an output user interface is configured to provide notification to a user. Processing circuitry is in communication with the input interface and the output interface, where the processing circuitry is configured to compare each of the triggering conditions to the
(Continued)

characterization data to identify a data transmission error. Upon identification of the data transmission error, the processing circuitry causes the output interface to present a query to the user.

18 Claims, 5 Drawing Sheets

(51) Int. Cl.
| | |
|---|---|
| *G16H 10/60* | (2018.01) |
| *G16H 40/67* | (2018.01) |
| *G06F 11/07* | (2006.01) |
| *G16H 40/60* | (2018.01) |
| *A61N 1/37* | (2006.01) |
| *H04L 29/08* | (2006.01) |
| *G06F 8/65* | (2018.01) |
| *A61N 1/372* | (2006.01) |
| *G16H 80/00* | (2018.01) |

(52) U.S. Cl.
CPC ...... *G06F 11/0778* (2013.01); *G06F 11/0784* (2013.01); *G16H 10/60* (2018.01); *G16H 40/60* (2018.01); *G16H 40/67* (2018.01); *H04L 29/08558* (2013.01); *A61N 1/37264* (2013.01); *G06F 8/65* (2013.01); *G16H 80/00* (2018.01); *H04L 67/12* (2013.01); *H04L 2209/88* (2013.01)

(58) Field of Classification Search
CPC ...... G16H 80/00; G06F 11/0766–0793; H04L 12/2803; H04L 12/2823; H04L 12/283; H04L 12/2834; H04L 12/66; H04L 29/06224; H04L 29/06251; H04L 29/06554; H04L 29/08558; H04L 29/08702; H04L 41/0273; H04L 41/06; H04L 61/6081; H04L 65/102; H04L 67/12; H04L 67/125; H04L 2209/88
See application file for complete search history.

(56) References Cited

U.S. PATENT DOCUMENTS

| | | | |
|---|---|---|---|
| 6,804,558 | B2 | 10/2004 | Haller et al. |
| 7,181,505 | B2 | 2/2007 | Haller et al. |
| 9,326,716 | B2 | 5/2016 | Heller et al. |
| 2003/0191376 | A1 | 10/2003 | Samuels et al. |
| 2005/0288601 | A1* | 12/2005 | Wood ............ A61B 5/486 600/513 |
| 2007/0056582 | A1* | 3/2007 | Wood ............ A61B 5/486 128/200.24 |
| 2011/0037586 | A1* | 2/2011 | Lu ............ G16H 40/20 340/539.1 |
| 2017/0055572 | A1* | 3/2017 | Utley ............ G16H 40/67 |

OTHER PUBLICATIONS

Varma, Niraj et al., "The Relationship Between Level of Adherence to Automatic Wireless Remote Monitoring and Survival in Pacemaker and Defibrillator Patients," Journal of the American College of Cardiology vol. 65, No. 24, 2015 (2601-2010) 10 pages.
"PRTG Network Monitor," Mar. 19, 2019 retrieved from URL <https://manuals.paessler.com/prtgmanual.pdf> on Apr. 2, 2019 (16 pages).
Paessler Ag, "Sensor States—PRTG Network Monitor," YouTube, Jan. 13, 2016, retrieved from URL < https://www.youtube.com/watch?v=MXH51E_B8Rc> on Apr. 1, 2019 (2 pages).
"International Search Report and Written Opinion," for PCT Application No. PCT/US2019/012324 dated Apr. 24, 2019 (12 pages).
"International Preliminary Report on Patentability," for PCT Application No. PCT/US2019/012324 dated Jul. 16, 2020 (8 pages).

* cited by examiner

TROUBLESHOOTING SYSTEM FOR REMOTE PATIENT MONITORING

This application claims the benefit of U.S. Provisional Application No. 62/613,687, filed Jan. 4, 2018, the content of which is herein incorporated by reference in its entirety.

FIELD OF THE TECHNOLOGY

The technology disclosed herein relates to a troubleshooting system. In particular, the technology disclosed herein relates to a troubleshooting system for a remote patient monitoring system.

BACKGROUND

Remote patient monitoring systems enable healthcare providers to remotely collect and assess patient physiological data. In such systems, one or more patient sensors are in indirect communication with a remote system that is accessible by the patient healthcare providers. Particularly, a communicator such as a repeater is placed in a patient's home. The communicator has a sensor interface that can download physiological data from the sensors and network interface that can upload that physiological data to a remote server, which is accessible by patient healthcare providers. The network can be a data communication network such as the Internet.

These remote patient monitoring systems have various advantages that ultimately correlate to reduced healthcare costs and improved patient outcomes. However, the adoption of and adherence to such systems can be improved. Some patients report never even setting up their communicator and, for some patients, the communicator stops working at some point, which the patient may or may not be aware of. As such, a system is needed to help improve the patient's ability to use and troubleshoot the remote patient monitoring system.

SUMMARY

Some embodiments of the technology disclosed herein relate to a troubleshooting system. A database defines a plurality of triggering conditions defining a data transmission error between a sensor and a remote location. A data transmission log is configured to receive characterization data defining each successful data transmission between a communicator and the remote location, where the characterization data is the time of a most recent successful data transmission, the type of sensor data transmitted in the most recent successful data transmission, and the timespan between successive data points in the sensor data transmitted in the most recent successful data transmission. An input user interface is configured to receive input from a user and an output user interface is configured to provide notification to a user. Processing circuitry is in communication with the input interface and the output interface, where the processing circuitry is configured to compare each of the triggering conditions to the characterization data to identify a data transmission error. Upon identification of the data transmission error, the processing circuitry causes the output interface to present a query to the user.

In some embodiments, upon receipt of characterization data of a successful data transmission, the processing circuitry causes the output user interface to provide a first notification to the user. Additionally or alternatively, the system has a timer configured to track a time period starting from the time of the most recent successful data transmission. Additionally or alternatively, a first triggering condition of the plurality of triggering conditions defines a time limit after a successful data transmission between the communicator and the remote location, and the processing circuitry is further configured to compare the time period to the time limit to identify the data transmission error. Additionally or alternatively, the output user interface has one or more of the following: an indicator light, a speaker, a display screen, and a paper communication.

Additionally or alternatively, the input user interface has one or more of: a keyboard, a microphone, and a touchscreen. Additionally or alternatively, the system has a patient communicator having a network interface and a sensor interface, whereby the patient communicator is configured to transmit data between the sensor and the remote location. Additionally or alternatively, the patient communicator is further configured to send the characterization data to the data transmission log. Additionally or alternatively, the patient communicator is configured to receive the characterization data from the remote location.

Additionally or alternatively, the processing circuitry is configured to provide a second notification to the user upon receipt of the user input, wherein the second notification is a suggestion to resolve the data transmission error. Additionally or alternatively, the user input provides a reason for a timing gap in transmitted data. Additionally or alternatively, a second triggering condition of the plurality of triggering conditions define sensor data outside an expected numeric range, and the characterization data further comprises a numeric range encompassing the sensor data transmitted in the most recent successful data transmission.

Some embodiments of the disclosed technology relate to a method. A plurality of triggering conditions are stored in a database, where each of the plurality of triggering conditions define a data transmission error between a sensor and a remote location. Characterization data is received by a data transmission log, where the characterization data defines each successful data transmission between a communicator and the remote location. The characterization data includes the time of a most recent successful data transmission, the type of sensor data transmitted in the most recent successful data transmission, and the timespan between successive data points within the sensor data transmitted in the most recent successful data transmission. Processing circuitry compares the triggering conditions to the characterization data to identify a data transmission error and causes an output user interface to present a query to a user upon identification of the data transmission error. An input user interface receives a user input in response to the query from a user.

In some embodiments, the processing circuitry causes the output user interface to provide a notification to the user upon receiving characterization data of a successful data transmission. Additionally or alternatively, a timer tracks a time period starting from the time of the last successful data transmission. Additionally or alternatively, the processing circuitry compares the time period to a first triggering condition of the plurality of triggering conditions to identify the data transmission error, where a first triggering condition defines a time limit after a successful data transmission between the communicator and the remote location.

Additionally or alternatively, a network interface and a sensor interface of a patient communicator transmits data between a sensor and a remote location. Additionally or alternatively, the patient communicator sends the characterization data to the data transmission log. Additionally or alternatively, a patient communicator receives the characterization data from the remote location. Additionally or alternatively, processing circuitry causes the output user interface to provide a second notification to the user upon receipt of the user input, wherein the second notification is a suggestion to resolve the data transmission error. Additionally or alternatively, the input user interface receives user input providing reason for a timing gap in transmitted data. Additionally or alternatively, a second triggering condition of the plurality of triggering conditions is defined, where the second triggering condition defines sensor data outside an expected numeric range. Additionally or alternatively, the characterization data also has a numeric range encompassing the sensor data transmitted in the most recent successful data transmission.

BRIEF DESCRIPTION OF THE DRAWINGS

The current technology may be more completely understood and appreciated in consideration of the following detailed description of various embodiments of the current technology in connection with the accompanying drawings.

DETAILED DESCRIPTION

The troubleshooting system disclosed herein is generally configured to help identify and resolve problems that may arise in a remote patient monitoring system. Errors within a remote patient monitoring system can limit the probative value of the data that is transmitted to the patient's health care providers, which reduces or eliminates the advantages of the remote patient monitoring system. Errors can include a user's inability to use and set-up the system, a user waiting too long to transmit data, a change in a user's Internet service provider, component software updates, adding new components, challenges during the setup process of various components, sensor calibration, sensor settings, environmental conditions, and the like. The troubleshooting system is configured to identify when an error has occurred and help direct the user to actions that will resolve the errors.

Figure 1:
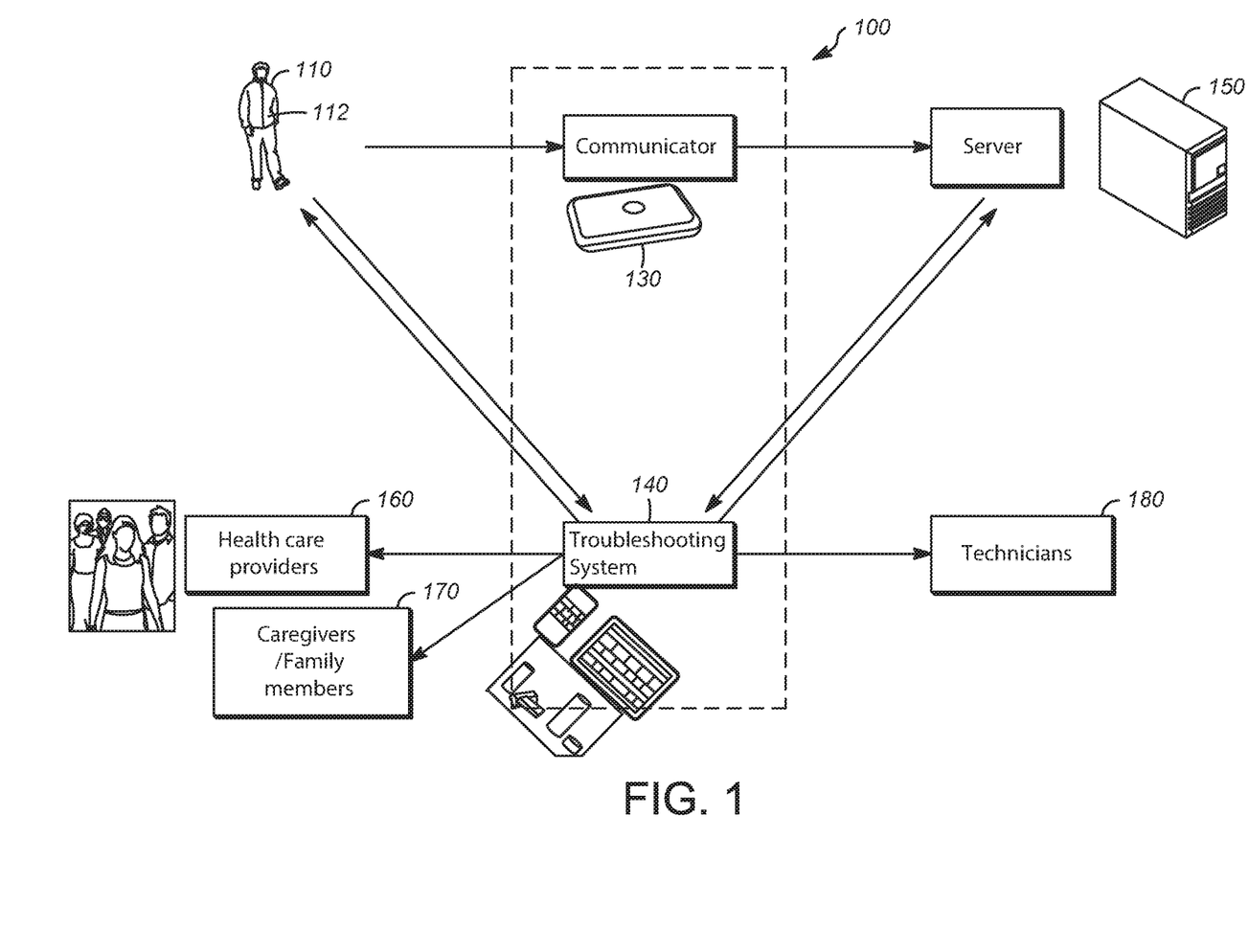
FIG. 1 is a schematic diagram of an example implementation of a remote patient monitoring system consistent with the technology disclosed herein.

FIG. 1 is a schematic diagram of an example implementation of a remote patient monitoring system consistent with the technology disclosed herein. The remote patient monitoring system 100 incorporates a troubleshooting system 140 to help setup and troubleshoot the system. The remote patient monitoring system 100 generally allows a patient 110 having a sensor 112 to be monitored by their health care providers 160 remotely. The sensor 112 is in communication with a communicator 130 which is in communication with a remote server 150 at a remote location. In particular, data from the sensor 112 is downloaded by the communicator 130 and uploaded to the remote server 150.

The communicator 130 has a sensor interface that is configured to establish data communication between the sensor 112 and the communicator 130. The communicator 130 has a network interface that is configured to establish data communication between the remote server 150 and the communicator. The communicator 130 is configured to transmit data between the sensor 112 and the remote server 150.

The sensor 112 is generally configured to sense patient physiological data and can be a plurality of sensors. In some embodiments, the sensor is implantable. In some embodiments, the sensor is a component of an implanted cardiac rhythm management device. In some embodiments, the sensor is an external sensor, such as a scale. Some example sensors contemplated by the current technology include blood pressure sensors, heart rate sensors, heart sound sensors, chemical sensors, accelerometers, respiratory sensors, and the like.

The troubleshooting system 140 is configured exchange data with both the sensor 112 of a patient 110 and the remote server 150. The troubleshooting system 140 can actively or passively receive data from the remote server 150 that characterizes the data transmission between the sensor 112 and the remote server 150 and upon identification of an error, the troubleshooting system 140 instructs/alerts the patient 110 of any actions that should be taken to resolve the error or asks the patient 110 for information which the troubleshooting system 140 can use to provide an instruction/alert to the patient 110. In some examples, characterization data is sent to the troubleshooting system 140 from the remote server 150. In other examples, the troubleshooting system 140 sends queries to the remote server 150 to retrieve the characterization data. The troubleshooting system 140 is also configured to provide instructions/alerts to other remote locations such as to the patient's healthcare providers 160, caregivers/family members 170, and/or technicians 180 for technical support.

The troubleshooting system 140 can be implemented in stand-alone hardware or, in some implementations, the troubleshooting system 140 is integrated with the communicator 130. In some embodiments, the troubleshooting system 140 can be implemented as an application in a smartphone or a home computer. In some embodiments, the troubleshooting system 140 can be part of the remote server 150. Other configurations are certainly contemplated. The functionality and structures mentioned in conjunction with FIG. 1 will be described in more detail with reference to the figures below.

Figure 2:
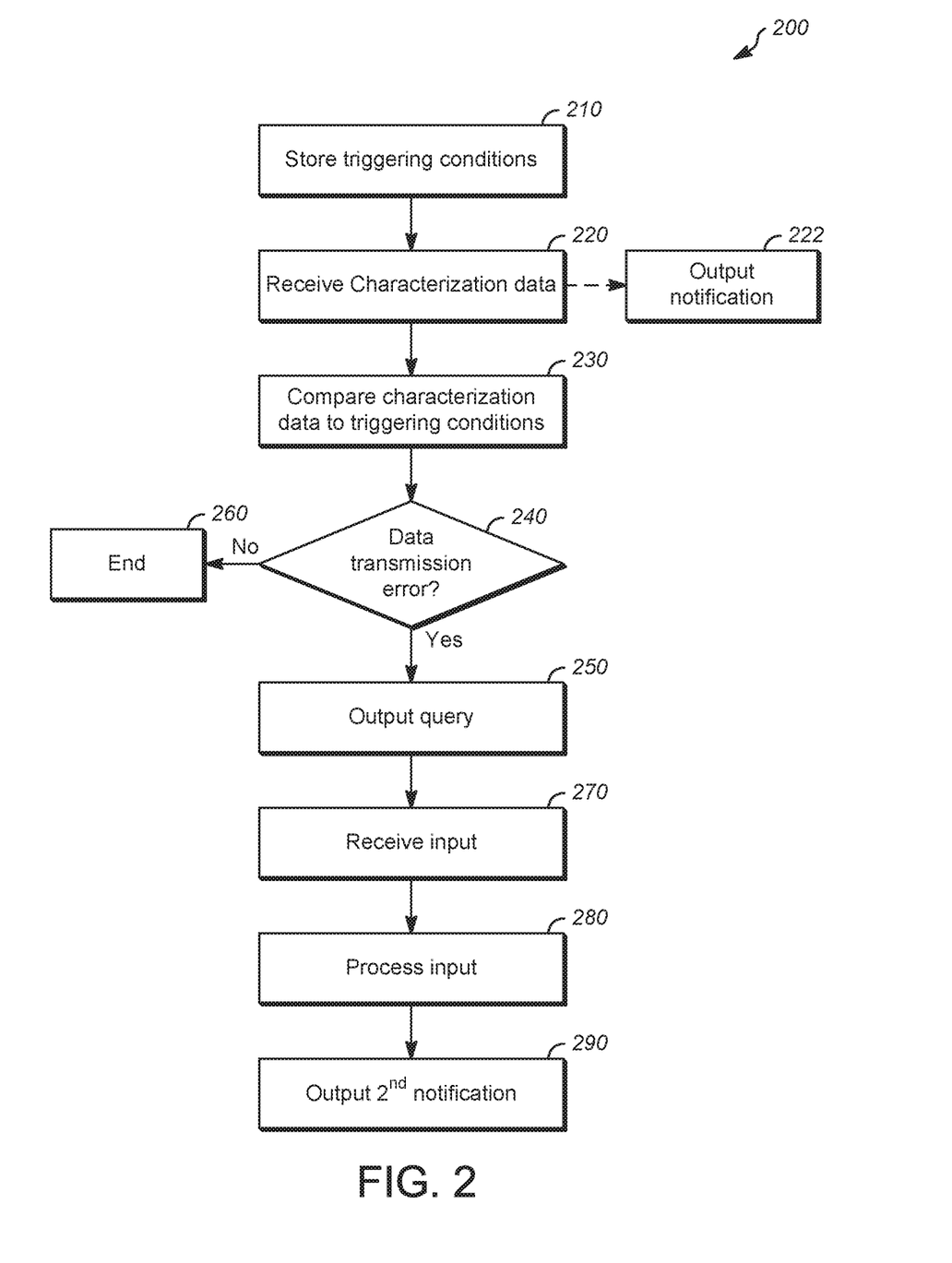
FIG. 2 is an example method executed by a troubleshooting system consistent with the technology disclosed herein.

FIG. 2 is an example method executed by an example troubleshooting system consistent with the technology disclosed herein. A plurality of triggering conditions is stored 210, wherein each of the triggering conditions define a data transmission error in sensor data transmission between a sensor and a remote location. The characterization data is received 220 that defines each successful data transmission between a communicator and the remote location. The troubleshooting system compares the characterization data to the triggering conditions 230 to identify a data transmission error 240. If a data transmission error is identified ("yes"), the troubleshooting system outputs a query 250. If a data transmission error is not identified ("no"), the method ends 260.

The characterization data can be received 220 by a data transmission log in memory of the troubleshooting system. The characterization data that is received 220 generally characterizes various aspects of each successful data transmission among the sensor, the communicator, and the remote location. For example, the time of the data transmission, the type of sensor data transmitted in the respective data transmission, and the timespan between successive data points within the sensor data transmitted in the respective data transmission are considered "characterization data" consistently with the technology disclosed herein. The characterization data is generally received 220 upon a successful data transmission. As such, the characterization data that is received characterizes the most recent successful data transmission. In some embodiments, the characterization data is non-sensitive data, meaning that the data is not subject to federal and/or local privacy laws governing patient data, e.g. personal data, protected health information, etc.

The characterization data that is received 220 can also define other aspects of the successful data transmission. In some examples, the characterization data includes a numeric range that encompasses the sensor data transmitted in the respective successful data transmission. In some examples, the characterization data includes the duration of the successful data transmission. In some examples, the characterization data includes the time between the most recent successful data transmission and the previous successful data transmission. In some examples, the characterization data includes the number of sensor readings within the sensor data transmitted in the respective successful data transmission.

In some, but not all embodiments, the processing circuitry of the troubleshooting system is configured to cause the output of a notification 222 upon receipt of characterization data 220 of a successful data transmission. The output of the notification 222 can be provided through an output user interface such as an indicator light, a speaker, a display screen, or even a paper communication, such as a print-out or a postal communication. In some examples, an indicator light illuminates to notify a user of a successful data transmission upon receipt of characterization data 220 of the successful data transmission. In some examples, a display screen notifies a user of a successful data transmission. In some examples, an audio signal is emitted to notify a user of the successful data transmission. In some examples, a postal communication is delivered to notify a user of the successful data transmission.

In some embodiments, the characterization data that is received 220 is generated at the remote location, such as by a remote server, but in some other embodiments the characterization data can be generated by components of the troubleshooting system. In some embodiments, a patient communicator can be configured to generate the characterization data. In some other embodiments, the patient communicator can receive the characterization data 220 from the remote location and relay the characterization data 220 to a data transmission log of the troubleshooting system. In some examples, the troubleshooting system can generate a portion of the characterization data. For example, the troubleshooting system can incorporate a timer that tracks a time period starting from the time of the most recent successful data transmission.

A successful data transmission as used herein is not synonymous with an error-free data transmission, although a successful data transmission would certainly encompass an error-free data transmission. Rather, a successful data transmission is defined as the establishment of a successful communication link between a communicator and a remote location, such as a remote server, so that some data is transmitted between the communicator and the remote location.

The plurality of stored triggering conditions 210 can be stored in a database in the troubleshooting system and can be programmed based on the requirements of the remote monitoring system. The plurality of stored triggering conditions 210 can be rules and algorithms that define when the troubleshooting system will identify a data transmission error between a sensor and a remote location based on the characterization data. For example, a triggering condition can define a time limit between successive successful data transmissions, or a time limit after a successful data transmission within which another successful data transmission is expected. As another example, a triggering condition can define the type(s) of sensor data that must be transmitted, such as blood pressure, heart rate, minute ventilation, accelerometer data, heart sounds, and the like. As another example, a triggering condition can define the maximum and/or minimum timespan between successive data points within transmitted sensor data. As another example, a triggering condition can define a maximum value, a minimum value, or otherwise define when the numeric sensor data falls outside of an expected numeric range. As yet another example, a triggering condition can define a maximum and/or minimum number of sensor readings within the transmitted sensor data.

Processing circuitry of the troubleshooting system can compare the received characterization data to the triggering conditions 230 to identify a data transmission error 240. For example, if the characterization data does not reflect that heart rate data was received, and the triggering data reflects that heart rate data is expected, then the troubleshooting system will identify a data transmission error 240. As another example, if the characterization data defines the time period starting from the time of the last successful data transmission and the triggering condition defines a time limit after a successful data transmission within which another successful data transmission is expected, then the troubleshooting system will identify a data transmission error 240 if the time period is greater than the time limit. Otherwise, if the troubleshooting system does not identify a data transmission error, then the process ends 260.

Upon identification of a data transmission error 240 by the processing circuitry, the system outputs a query 250 to a user. The processing circuitry can cause an output user interface to provide the query 250. The output user interface can be a speaker or a display screen that is configured to query a user 250. The query is generally configured to elicit information from the user about the system. For example, if the most recent successful data transmission occurred outside of an expected time period from the previous successful data transmission, the query can request the user provide a reason for the timing gap. As another example, if data from a particular sensor was not transmitted to the remote location, the query can request the user perform a testing operation on the sensor or the communicator. Other example queries will be discussed herein.

In some embodiments, the troubleshooting system outputs a notification to the user that is indicative of the severity of the data transmission errors identified. For example, the troubleshooting system can display color-coded lights, such as green, yellow/orange, and red. In such an example, a green light can indicate that there have been no, or very minor, data transmission errors, a yellow/orange light can indicate that there are data transmission errors related to gaps in data, such as missing portions of non-critical data, and a red light can indicate that there is critical data missing. In such embodiments, a user is kept on notice regarding the overall health of the remote monitoring system. In such embodiments, the user can provide an input to the troubleshooting system to initiate troubleshooting functionality.

The troubleshooting system will generally receive an input from the user 270 in response to the query 250 through an input user interface such as a microphone, a keyboard, or a touchscreen. The processing circuitry of the troubleshooting system processes the user input 280 to troubleshoot the data transmission error. In some embodiments, the input received 270 can resolve the data transmission error. Using an example from the paragraph above, if the input from the user 270 indicates that a timing gap in transmitted data is due to the patient being on vacation, the processing circuitry of the troubleshooting system can interpret that input to determine that no further action need be taken to resolve the error in data transmission. In some other embodiments, the input received 270 can enable the troubleshooting system to further troubleshoot the data transmission error, which will be described in more detail below.

After processing the user input 280, the processing circuitry of the troubleshooting system can cause an output user interface to provide a second notification to the user 290. The second notification can communicate that the data transmission error is resolved based on the input received. The second notification can communicate a suggestion to resolve the data transmission error, such as instructing the user to calibrate particular sensors, instructing the user to set up a new component, or re-set an existing component. The second notification can also communicate that the user should contact a particular person/entity for support, such as healthcare providers or technical support.

In some embodiments, the troubleshooting system is configured to send notifications through a network interface to a remote location, such as to the remote server, technicians, healthcare providers, family members of the user, and the like. The notifications can be through e-mail, postal communication, website notifications, automated telephone calls, and the like.

Figure 3:
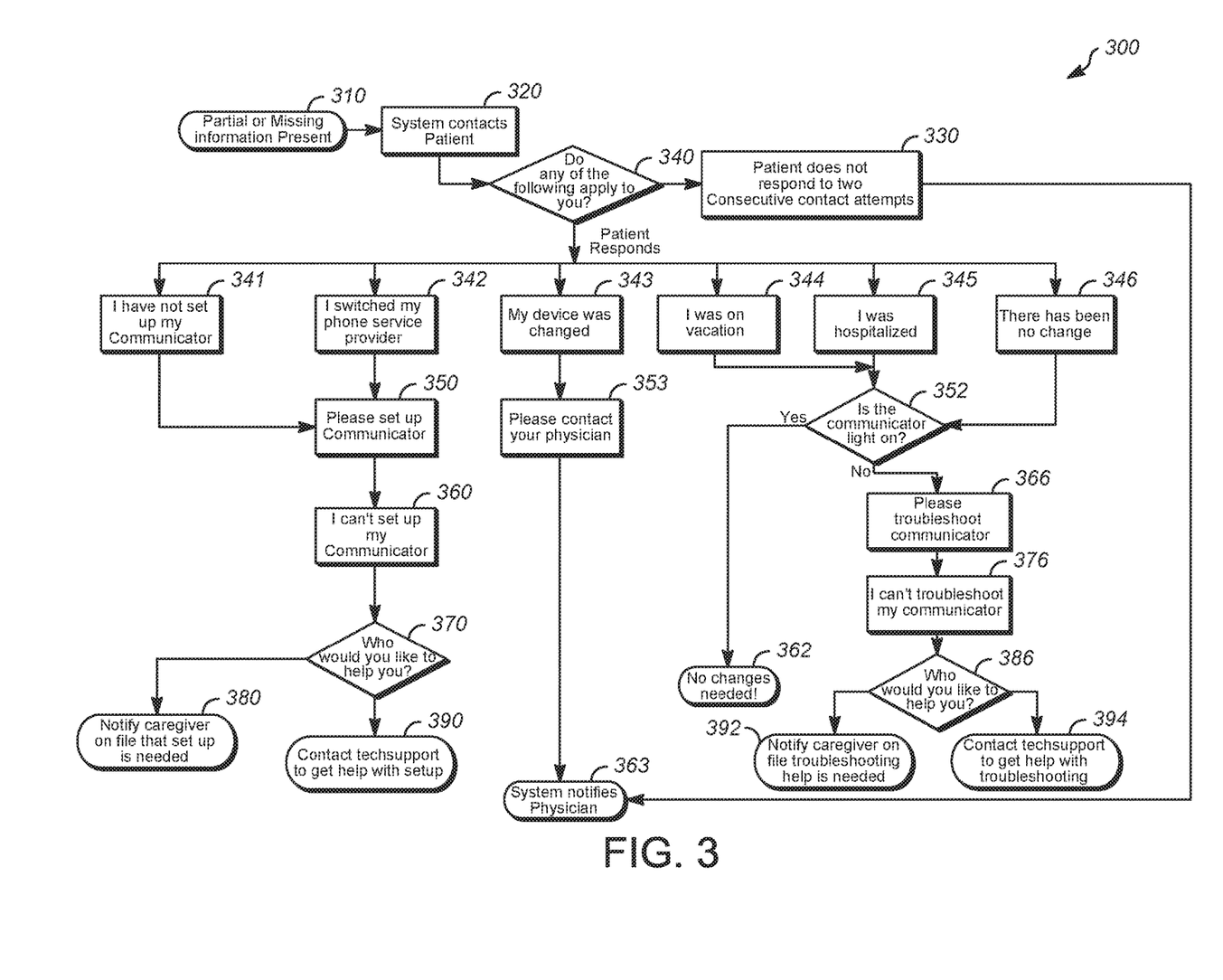
FIG. 3 is another example method of troubleshooting a remote patient monitoring system consistent with the technology disclosed herein.

FIG. 3 is an example implementation of a method 300 associated with a remote patient monitoring system consistent with the technology disclosed herein. The method 300 can be executed upon a successful data transmission. In this example, system identifies a data transmission error that is missing portions of data 310. The system attempts to contact the patient 320 and provides a query 340. If the system receives no response after two attempts 330, the system notifies the patient's physician 363. The system can receive a number of responses from the patient 341, 342, 343, 344, 345, 346.

The system's attempt to contact the patient 320 can be a notification, such as an audio or visual indicator and/or the query 340 itself. They query 340 can be presented on a display screen. In this example, the system asks 340 the patient whether any particular situation applies out of a number of possible situations, which can be presented on a display screen, for example. A user can provide an input through an input user interface, such as those described above, to provide a response. The input can provide a reason for a timing gap in the data, for example. Based on the user input, the system can provide a second notification to the user that is a suggestion to resolve the data transmission error.

In the current example, if the user inputs that the communicator has not been set up 341, or that they switched phone service providers 324, the system can advise the patient to set up the communicator 350 through the output user interface. The system can provide an option to the user that allows the user to provide an input to the system that communicates to the system that s/he cannot setup the communicator 360 for some reason. Upon receiving such an input, the system can further query the patient regarding who s/he would like to contact to provide assistance 370. The patient can elect to contact a caregiver, upon which the system sends a notification to the caregiver that setup is needed 380. The patient can also elect to contact technical support, upon which the system sends a notification to technical support that setup help is needed 390. Notifications can be sent to other individuals or entities, as well.

If a user indicates that the medical device has been changed 343, the system notifies the user to contact the physician 353 and, in many embodiments, the system is configured to receive a user input that instructs the system to notify the physician or other caregiver. The system can then notify the physician 363.

A user can provide an input that s/he was on vacation 344, was hospitalized 345, or that there has been no change 346. Upon receiving such inputs, the system can provide a second query to the user regarding whether the communicator light is on 352. The user can provide an input that indicates "yes, the light is on" or "no, the light is not on." If the user inputs data indicating that the light is on, the system can provide a notification to the user that no changes are needed 362. However, if the user inputs data indicating that the communicator light is not on, the system can notify the user to troubleshoot the communicator 366. In some embodiments, the system can provide troubleshooting assistance, such as by providing outputs that suggest further troubleshooting steps that the patient can take. The user can provide an input to the system that s/he is unable to troubleshoot the communicator 376, and in response the system can further query the patient regarding who s/he would like to contact to provide assistance 386. The patient can elect to contact a caregiver, upon which the system sends a notification to the caregiver that troubleshooting help is needed 392. The patient can also elect to contact technical support, upon which the system sends a notification to technical support that troubleshooting help is needed 394. Notifications can be sent to other individuals or entities, as well.

Figure 4:
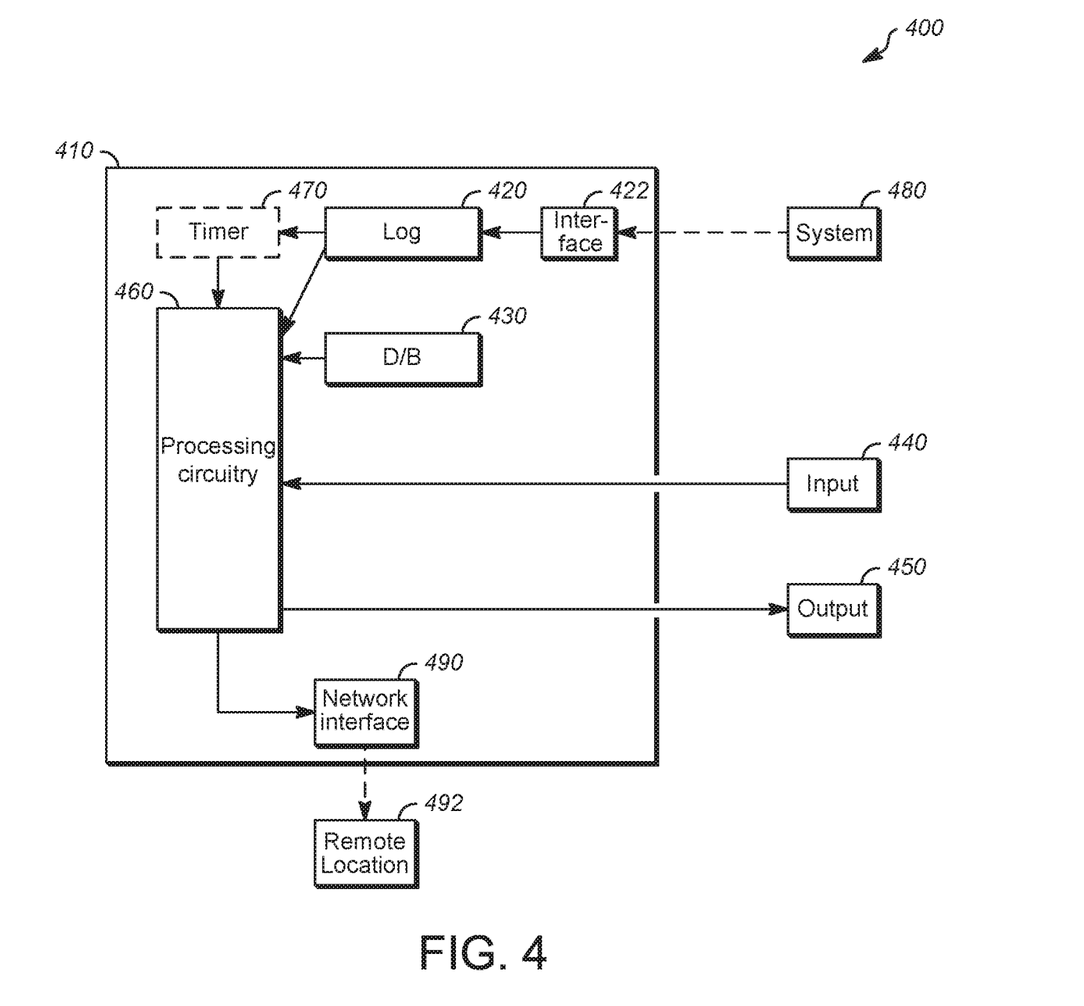
FIG. 4 is an example troubleshooting system consistent with the technology disclosed herein.

FIG. 4 is an example troubleshooting system consistent with the technology disclosed herein. The troubleshooting system 400 has a housing 410 that generally contains at least a portion of the system components. The troubleshooting system 400 has a database 430, a data transmission log 420, processing circuitry 460, an input user interface 440 and an output user interface 450.

The database 430 defines a plurality of triggering conditions defining a data transmission error between a sensor and a remote location. Triggering conditions are consistent with those described above with FIG. 2.

The data transmission log 420 is configured to receive characterization data defining each successful data transmission between a communicator and the remote location. Characterization data is generally consistent with that described above in accordance with FIG. 2. In various embodiments, the characterization data can include the time of a most recent successful data transmission, such as a timestamp. The characterization data can also include the type of sensor data transmitted in the most recent successful data transmission, such as the make and model of the sensor, or the specific physiological measure that is being measured by the sensor. The characterization data can also include the timespan between successive data points in the sensor data transmitted in the most recent successful data transmission. In some embodiments, the timespan between successive data points in the sensor data reflect the maximum and/or minimum timespans between successive data points in the transmitted sensor to reduce the volume of data. The data transmission log 420 can be populated by a component external to the system 480 such as a remote server at the remote location or, in some embodiments, a communicator that can be local to or remote from the troubleshooting system 400. In such embodiments, the troubleshooting system 400 can have a data receiving interface 422 that is configured to receive such characterization data. In some other embodiments, the characterization data can be generated by the troubleshooting system 400 itself.

The input user interface 440 is configured to receive input from a user and can be consistent with input user interfaces described above in conjunction with the discussion of FIG. 2. Similarly, the output user interface 450 is configured to provide a notification to the user and can be consistent with output user interfaces described above in conjunction with the discussion of FIG. 2.

The processing circuitry 460 is in communication with the input user interface 440 and the output user interface 450. The processing circuitry 460 is also in communication with the data transmission log 420 and the database 430. The processing circuitry is configured to compare the triggering conditions stored in the database 430 to the characterization data in the data transmission log 420 to identify a data transmission error. Upon identification of the data transmission error, the processing circuitry 460 causes the output user interface 450 to present a query to the user. The query can be consistent with those described above with reference to FIG. 2.

The troubleshooting system 400 can also have a network interface 490 in communication with the processing circuitry 460 such that notifications can be sent to a remote location 492. In some embodiments, where the troubleshooting system 400 incorporates a data receiving interface 422, the network interface 490 and the data receiving interface 422 can be a single component.

In some, but not all embodiments, the troubleshooting system 400 can incorporate a timer 470 that is configured to track a time period starting from the time of the most recent successful data transmission. In such embodiments, the database 430 can define a time limit after a successful data transmission between the communicator and the remote location and the processing circuitry can be configured to compare the time period to the time limit to identify a data transmission error. In some embodiments, the troubleshooting system 400 does not have a timer, and the characterization data in the data transmission log 420 defines the time period between the last successful data transmission and the most recent successful data transmission.

Figure 5:
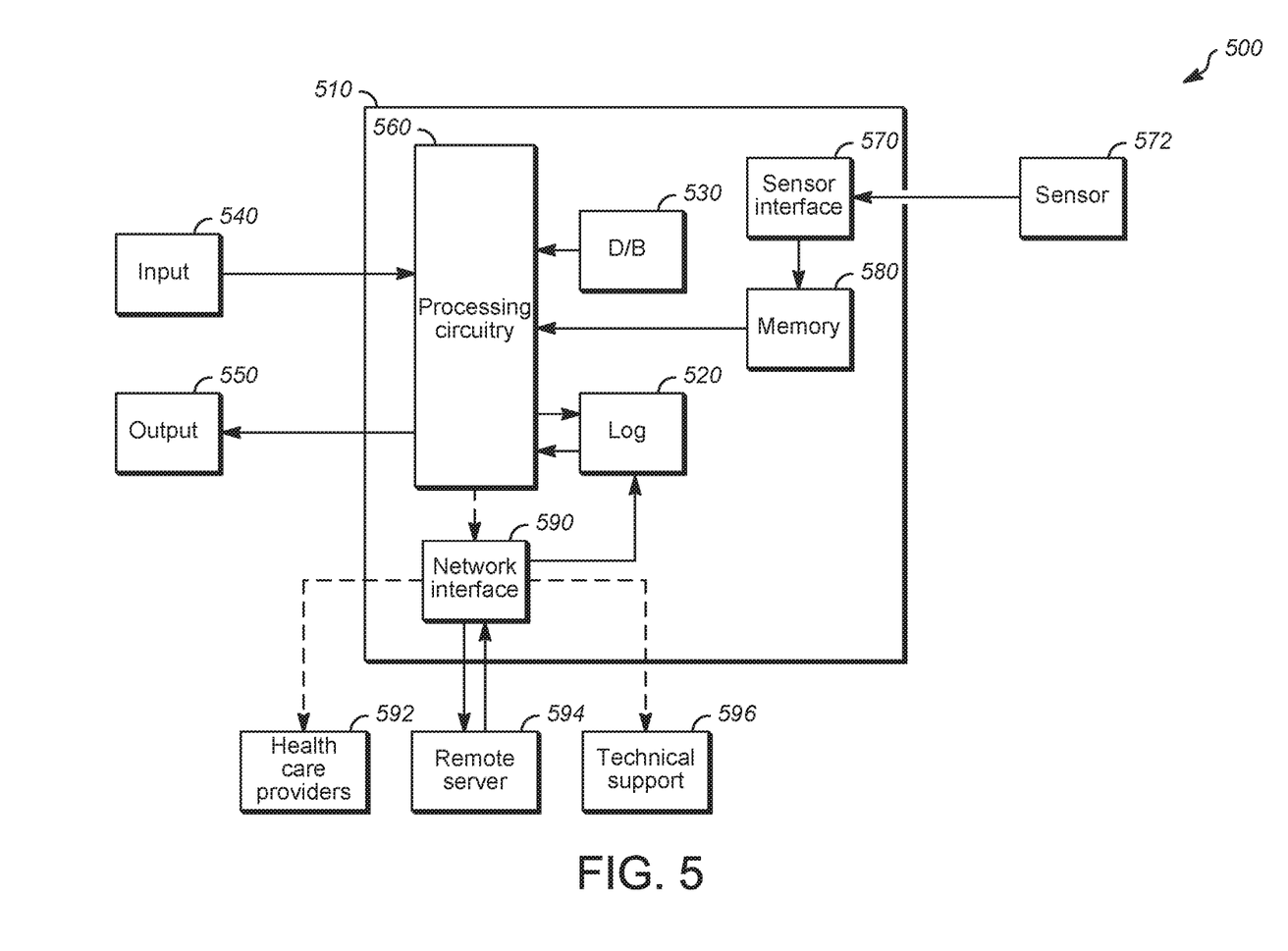
FIG. 5 is another example implementation of the technology disclosed herein.

FIG. 5 is another example implementation of the technology disclosed herein, where components of the troubleshooting system are incorporated in a patient communicator 500. The patient communicator 500 has a housing 510 that houses various components. A sensor interface 570 is configured to communicably couple to a sensor 572 to download patient physiological data from the sensor 572. The sensor interface 570 can define a wired or wireless communication link with the sensor 572. In some embodiments, the sensor interface 570 can incorporate short-range or long-range radio frequency telemetry circuitry, inductive telemetry circuitry, or other types of communication hardware. The physiological data can be saved in memory 580 either on a permanent basis, or temporarily until processing circuitry 560 causes the data to be sent via a network interface 590 to a remote server 594.

The remote server 594 can be configured to perform data analysis of the patient physiological data and, in some embodiments, generate characterization data associated with the successful data transmission between the communicator 500 and the remote server 594. The remote server 594 can send the characterization data to the communicator 500 via the network interface 590, which can be stored by a data transmission log 520 in the communicator 500. The processing circuitry 560 can compare the data in the data transmission log 520 with triggering conditions stored in a database 530 to identify whether a data transmission error has occurred.

An output user interface 550 is in communication with the processing circuitry 560 and is directed, by the processing circuitry, to provide a query to a user upon identification of a data transmission error. The output user interface 550 can also be directed, by the processing circuitry, to notify a user upon a successful data transmission between the communicator 500 and the remote server 594. The output user interface 550 can also be directed, by the processing circuitry, to provide a notification to a user that is a recommendation, notification, instruction, or further query relevant to resolving the data transmission error, as has been described earlier.

An input user interface 540 is also in communication with the processing circuitry 560 and is configured to receive an input from the user. The input from the user can be an answer to a query presented by the output user interface 550. The processing circuitry 560 is configured to process the user input to resolve or further troubleshoot the data transmission error.

In some embodiments, the network interface 590 is configured to establish communications with other remote locations to send notifications. Remote locations can include the user's healthcare providers 592, technical support 596 for the remote monitoring system, caregivers, family members, and the like. The processing circuitry 560 can be configured to determine what party to send the notification to and what the notification is. In some embodiments, user input through the input user interface 540 can specify a party to send a notification to, and even the information that the notification communicates. For example, in some embodiments the user can specify that they would like to contact technical support 596 for troubleshooting of the remote monitoring system. In such an embodiment, the processing circuitry 560 can execute those specifications.

It should also be noted that, as used in this specification and the appended claims, the phrase "configured" describes a system, apparatus, or other structure that is constructed to perform a particular task or adopt particular characteristics. The phrase "configured" can be used interchangeably with other similar phrases such as "arranged", "arranged and configured", "constructed and arranged", "programmed", "manufactured and arranged", and the like. Various steps of the processes disclosed and described herein can be stored as program instructions on a non-transitory computer-readable storage medium that are configured to be executed by a processor.

All publications and patent applications in this specification are indicative of the level of ordinary skill in the art to which the present technology pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive.

We claim:

1. A system comprising:
   a database defining a plurality of triggering conditions defining a data transmission error in sensor data transmission between a sensor and a remote location;
   a communicator comprising a network interface and a sensor interface, whereby the communicator is configured to transmit data between the sensor and the remote location;
   a data transmission log configured to receive characterization data defining each successful data transmission between the communicator and the remote location, wherein the characterization data comprises the time of a most recent successful data transmission, the type of sensor data transmitted in the most recent successful data transmission, and a timespan between successive data points in the sensor data transmitted in the most recent successful data transmission;
   an input user interface and an output user interface, wherein the input user interface is configured to receive input from a user and the output user interface is configured to provide notification to a user; and
   processing circuitry in communication with the input user interface and the output user interface, wherein the processing circuitry is configured to compare each of the triggering conditions to the characterization data to identify a data transmission error, and wherein upon identification of the data transmission error, the processing circuitry causes the output interface to present a query to the user;
   wherein the communicator is further configured to send the characterization data to the data transmission log.

2. The system of claim 1, wherein, upon receipt of characterization data of a successful data transmission, the processing circuitry causes the output user interface to provide a first notification to the user.

3. The system of claim 1, further comprising a timer configured to track a time period starting from the time of the most recent successful data transmission.

4. The system of claim 3, wherein a first triggering condition of the plurality of triggering conditions defines a time limit after a successful data transmission between the communicator and the remote location, and the processing circuitry is further configured to compare the time period to the time limit to identify the data transmission error.

5. The system of claim 1, wherein the output user interface comprises one or more of the following: an indicator light, a speaker, a display screen, and a paper communication.

6. The system of claim 1, wherein the input user interface comprises one or more in the group consisting of: a keyboard, a microphone, and a touchscreen.

7. The system of claim 1, wherein the communicator is configured to receive the characterization data from the remote location.

8. The system of claim 1, wherein the processing circuitry is configured to provide a second notification to the user upon receipt of the user input, wherein the second notification is a suggestion to resolve the data transmission error.

9. The system of claim 8, wherein the user input provides a reason for a timing gap in transmitted data.

10. The system of claim 9, wherein a second triggering condition of the plurality of triggering conditions define sensor data outside an expected numeric range, and the characterization data further comprises a numeric range encompassing the sensor data transmitted in the most recent successful data transmission.

11. A method comprising:
    storing a plurality of triggering conditions in a database, wherein each of the plurality of triggering conditions define a data transmission error in sensor data transmission between a sensor and a remote location;
    receiving characterization data in a data transmission log, wherein the characterization data defines each successful data transmission between a communicator and the remote location, wherein the characterization data comprises the time of a most recent successful data transmission, the type of sensor data transmitted in the most recent successful data transmission, and the timespan between successive data points within the sensor data transmitted in the most recent successful data transmission;
    transmitting data between a sensor and a remote location using a network interface and a sensor interface of the communicator; and the communicator sending the characterization data to the data transmission log;
    comparing, by processing circuitry, the triggering conditions to the characterization data to identify a data transmission error;
    the processing circuitry causing an output user interface to present a query to a user upon identification of the data transmission error; and
    an input user interface receiving a user input in response to the query from a user.

12. The method of claim 11 further comprising the processing circuitry causing the output user interface to provide a notification to the user upon receiving characterization data of a successful data transmission.

13. The method of claim 11, further comprising tracking a time period, by a timer, starting from the time of the last successful data transmission.

14. The method of claim 13, further comprising the processing circuitry comparing the time period to a first triggering condition of the plurality of triggering conditions to identify the data transmission error, wherein a first triggering condition defines a time limit after a successful data transmission between the communicator and the remote location.

15. The method of claim 11, further comprising the communicator receiving the characterization data from the remote location.

16. The method of claim 11, further comprising processing circuitry causing the output user interface to provide a second notification to the user upon receipt of the user input, wherein the second notification is a suggestion to resolve the data transmission error.

17. The method of claim 16, further comprising receiving, from the input user interface, user input providing reason for a timing gap in transmitted data.

18. The method of claim 17, further comprising defining a second triggering condition of the plurality of triggering conditions, wherein the second triggering condition defines sensor data outside an expected numeric range, and the characterization data further comprises a numeric range encompassing the sensor data transmitted in the most recent successful data transmission.

* * * * *